United States Patent [19]

Bock et al.

[11] Patent Number: 4,559,339

[45] Date of Patent: Dec. 17, 1985

[54] INDOL-3-YL-QUINAZOLINO-1,4-BEN-ZODIAZEPIN-5,13-DIONES

[75] Inventors: Mark G. Bock; Roger M. Freidinger, both of Hatfield; Ben E. Evans, Lansdale, all of Pa.

[73] Assignee: Merck & Co., Inc., Rahway, N.J.

[21] Appl. No.: 695,118

[22] Filed: Jan. 25, 1985

[51] Int. Cl.$^4$ .................. A61K 31/55; C07D 403/14
[52] U.S. Cl. ............................ 514/219; 260/239.3 P
[58] Field of Search ................. 260/239.3 P; 424/251; 514/219

[56] References Cited

U.S. PATENT DOCUMENTS 3,651,046 3/1972 Derieg et al. ............... 260/239.3 P
4,187,307 2/1980 Mayer et al. ................ 260/239.3 P Primary Examiner—Robert T. Bond
Attorney, Agent, or Firm—Richard A. Elder; Hesna J. Pfeiffer; Daniel T. Szura

[57] ABSTRACT

Novel indol-3-yl-quinazolino-1,4-benzodiazepin-5,13-diones, which are antagonists of the function of cholecystokinins (CCK), to the preparation of these compounds from compounds prepared by aerobic fermentation of certain *Aspergillus alliaceus* strains, and to the use of these compounds to antagonize the function of CCK, which antagonism is useful, e.g., for the treatment and prevention of disorders of the gastrointestinal, central nervous and appetite-regulatory systems of mammals, especially of humans.

17 Claims, No Drawings

INDOL-3-YL-QUINAZOLINO-1,4-BENZODIAZEPIN-5,13-DIONES

The present invention is directed to novel indol-3-yl-quinazolino-1,4-benzodiazepin-5,13-diones, which are antagonists of the function of cholecystokinins (CCK), to the preparation of these compounds, and to the use of these compounds to antagonize the function of CCK, which antagonism is useful, e.g., for the treatment and prevention of disorders of the gastrointestinal, central nervous and appetite regulatory systems of mammals, especially of humans.

BACKGROUND OF THE INVENTION

Cholecystokinins (CCK) are neuropeptides (see, Mutt and Jorpes, *Biochem. J.*, 125, 678 (1971)) which exist in both gastrointestinal tissue and the central nervous system (V. Mutt, *Gastrointestinal Hormones*, G. B. J. Glass, ed., Raven Press, N.Y., 1980, p. 169), and include, e.g., CCK-33, a neuropeptide of thirty-three amino acids and its carboxyl terminal octapeptide, CCK-8. These molecules are believed to be physiological satiety hormones and, therefore, may play an important role in appetite regulation (G. P. Smith, *Eating and Its Disorders*, A. J. Stunkard and E. Stellar, Eds., Raven Press, New York, 1984, p. 67).

In addition, CCK's stimulate colonic motility, gall bladder contraction, and pancreatic enzyme secretion, and inhibit gastric emptying. CCK's reportedly also co-exist with dopamine in certain mid-brain neurons, and thus may additionally play a role in the functioning of dopaminergic systems in the brain, as well as serve as neurotransmitters in their own right. See: A. J. Prange et al., "Peptides in the Central Nervous System", *Ann. Repts. Med. Chem.*, 17, 31, 33 (1982), and references cited therein; J. A. Williams, *Biomed. Res.*, 3, 107 (1982); and J. E. Morley, *Life Sci.*, 30, 479 (1982).

Antagonists to CCK have been useful for preventing or treating CCK-related disorders of the gastrointestinal, central nervous and appetite-regulatory systems of mammals, especially of humans. Three distinct chemical classes of CCK-receptor antagonists have been reported. The first class comprises derivatives of cyclic nucleotides, of which dibutyryl cyclic GMP has been shown to be the most potent by detailed structure-function studies (see, N. Barlos et al., *Am. J. Physiol.*, 242, G161 (1982) and P. Robberecht et al., *Mol. Pharmacol.*, 17, 268 (1980)). The second class comprises peptide antagonists which are C-terminal fragments and analogs of CCK, of which both shorter (Boc-Met-Asp-Phe-NH$_2$, Met-Asp-Phe-NH$_2$) and longer (Cbz-Tyr(SO$_3$H)-Met-Gly-Trp-Met-Asp-NH$_2$) C-terminal fragments of CCK can function as CCK-antagonists, according to recent structure-function studies (see, R. T. Jensen et al., *Biochim. Biophys. Acta.*, 757, 250 (1983), and M. Spanarkel et al., *J. Biol. Chem.*, 258, 6746 (1983)). Then, the third class of CCK receptor antagonists comprises the amino acid derivatives: proglumide, a derivative of glutaramic acid, and the N-acyl tryptophans, including para-chlorobenzoyl-L-tryptophan (benzotript), (see, W. F. Hahne et al., *Proc. Natl. Acad. Sci. U.S.A.*, 78, 6304 (1981) and R. T. Jensen et al., *Biochim. Biophys. Acta.*, 761, 269 (1983)). All of these compounds, however, are relatively weak antagonists of CCK (IC$_{50}$: generally $10^{-4}$M, but down to $10^{31\ 6}$M in the case of the peptides) and the peptide CCK-antagonists have substantial stability and absorption problems.

The compound, 7β-[(1H-indol-3-yl)methyl]-quinazolino(3,2-A) (1,4)benzodiazepin-5,13(6H,7H)dione, of the formula (I):

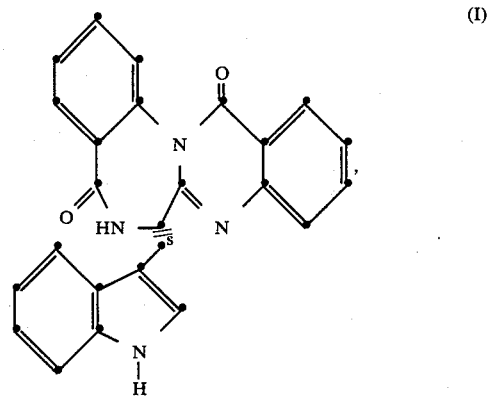

which is produced in a controlled aerobic fermentation of a strain of *Aspergillus alliaceus* Thom and Church, preferably strain ATCC No. 20655 or strain ATCC No. 20656, as disclosed in U.S. application, Ser. No. 509,883, filed Sept. 20, 1983, now U.S. Pat. No. 4,530,790 has been shown to be a CCK-antagonist. This compound is, however, selective in inhibiting the function of cholecystokinins in the gut (IC$_{50}$=26 μM by pancreas assay).

It was, therefore, an object of this invention to identify substances which demonstrate more balanced selectivity versus the compound, 7β-[(1H-indol-3-yl)methyl]quinazolino(3,2-A) (1,4) benzodiazepin-5,13-(6H,7H)dione, in antagonizing the function of cholecystokinins in both the brain and the gut in disease states in mammals, especially in humans. It was another object of this invention to develop a method of preparing these novel cholecystokinin-antagonists. It was also an object of this invention to develop a method of antagonizing the function of cholecystokinins in disease states in mammals. It was still a further object of this invention to develop a method of preventing or treating disorders of the gastrointestinal, central nervous and appetite regulatory systems of mammals, especially of humans.

SUMMARY OF THE INVENTION

The instant invention is directed to certain indol-3-yl-quinazolino-1,4-benzodiazepin-5,13-diones. These compounds are antagonists of the function of cholecystokinins (CCK). This invention also relates to the preparation of these compounds from compounds prepared by aerobic fermentation of certain *Aspergillus alliaceus* strains, and to the use of these compounds in the treatment and prevention of disorders of the gastrointestinal, central nervous and appetite regulatory systems of mammals, especially of humans.

DETAILED DESCRIPTION OF THE INVENTION

The indol-3-yl quinazolino-1,4-benzodiazepin-5,13-diones of this invention are compounds of the formula (II):

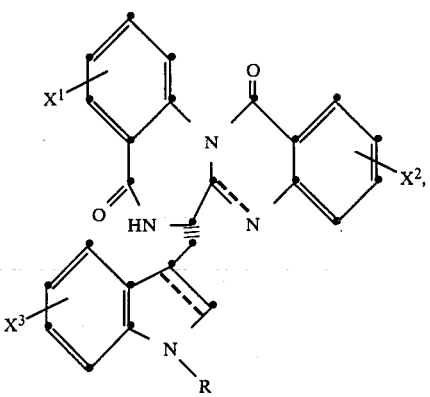

(II)

wherein:

$X^1$, $X^2$ and $X^3$ are independently H, Br, Cl, F, OH, $C_1$-$C_4$-alkyl, O—$C_1$-$C_4$-alkyl or

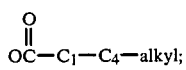

R is H; $C_1$-$C_8$-straight- or branched-chain alkyl; $C_3$-$C_8$-cyclic alkyl; $C_1$-$C_8$-straight- or branched-chain aralkyl, where the aryl is, for example, phenyl or naphthyl, which is unsubstituted or is monosubstituted on the aromatic ring by Br, Cl, F, OH, O—$C_1$-$C_4$-alkyl,

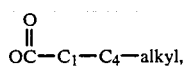

$NO_2$, $NH_2$, $C_1$-$C_4$-alkyl, CN or $CF_3$;

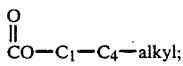

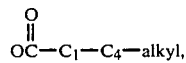

where the substituent is Br, Cl, F, OH, O—$C_1$-$C_4$-alkyl,

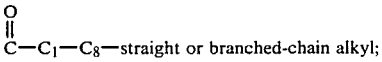

$NO_2$, $NH_2$, $C_1$-$C_4$-alkyl, CN, or $CF_3$;

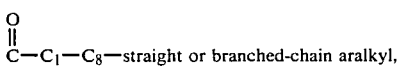

where the aryl is, for example, phenyl or naphthyl, which is unsubstituted or is monosubstituted on the aromatic ring by Br, Cl, F, OH, O—$C_1$-$C_4$-alkyl,

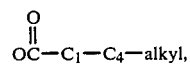

$NO_2$, $NH_2$, $C_1$-$C_4$-alkyl, CN or $CF_3$;

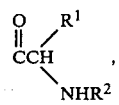

where $R^1$ is H; $C_1$-$C_4$-straight or branched-chain alkyl; $CH_2$-unsubstituted or monosubstituted phenyl, wherein the substituent is Br, Cl, F, OH, O—$C_1$-$C_4$-alkyl, O—$CH_2$-phenyl, or

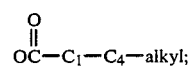

$CH_2$-3-indole; $CH_2$-imidazole; $CH_2CH_2SCH_3$;

hydroxy-$C_1$-$C_4$-alkyl; $(CH_2)_n NH_2$; or

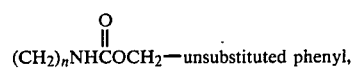

wherein n is 1 to 4; and $R^2$ is H, CO—$C_1$-$C_4$-straight or branched-chain alkyl, or

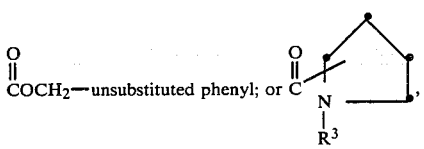

where $R^3$ is H,

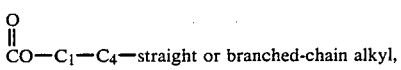

or

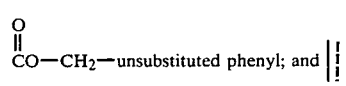

is a variable (saturated [single] or unsaturated [double]) bond;
or pharmaceutically-acceptable salts of these compounds.

Preferred compounds of formula II, according to the instant invention, include those in which $X^1$, $X^2$ and $X^3$ are H; R is $$\overset{O}{\underset{}{\overset{\|}{C}}}CHR^1NHR^2,$$

wherein $R^1$ is $CH_2CH(CH_3)_2$ and $R^2$ is

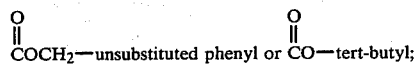

and the variable bonds are either both saturated (single) or one is saturated and the other is unsaturated (double), and pharmaceutically-acceptable salts thereof. These preferred compounds include 7,7A-dihydro-7-(1H-indol-3-yl)-methylquinazolino(3,2-B)-1,4-benzodiazepin-5,13-(6H,9H)-dione; 7-[(2,3-dihydro-1H-indol-3-yl)methyl]-quinazolino(3,2-A)-1,4-benzodiazepin-5,13-(6H,7H)-dione; 7-[(1-[2(S)-((1,1-dimethylethoxy)carbonyl)-amino-4-methylpentanoyl]-1H-indol-3-yl)methyl]-quinazolino(3,2-A)-1,4-benzodiazepin-5,13-(6H,7H)-dione; 7-[(1-[2(S)-((1,1-dimethylethoxy)carbonyl)-amino-4-methylpentanoyl]-2,3-dihydro-1H-indol-3-yl)-methyl]quinazolino-(3,2-A)-1,4-benzodiazepin-5,13-(6H,7H)-dione; 7-[(1-[2(S)-((1,1-dimethylethoxy)-carbonyl)amino-4-methylpentanoyl]-2,3-dihydro-1H-indol-3-yl)methyl]quinazolino(3,2-A)-1,4-benzodiazepin-5,13-(5H,7H)-dione; 7-[(1-[2(R)-((1,1-dimethylethoxy)carbonyl)amino-4-methylpentanoyl]-2,3-dihydro-1H-indol-3-yl)methyl]quinazolino(3,2-A)-1,4-benzodiazepin-5,13-(6H,7H)-dione; 7-[(1-[2(R)-((1,1-dimethylethoxy)carbonyl)amino-4-methylpentanoyl]-2,3-dihydro-1H-indol-3-yl)methyl]quinazolino(3,2-A)-1,4-benzodiazepin-5,13-(5H,7H)-dione; and 7-[(1-[2(S)-phenylmethoxycarbonylamino-4-methylpentanoyl]-1H-indol-3-yl)methyl]quinazolino-(3,2-B)-1,4-benzodiazepin-5,13-(6H,7H)-dione.

Particularly preferred compounds according to the instant invention include those wherein $X^1$, $X^2$ and $X^3$ are H; R is

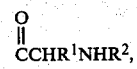

wherein $R^1$ is $CH_2CH(CH_3)_2$ and $R^2$ is

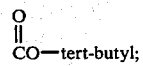

and the variable bonds are either bond saturated or one is saturated and the other is unsaturated, and pharmaceutically-acceptable salts thereof. These compounds include 7-[(1-[2(R)-((1,1-dimethylethoxy)carbonyl)amino-4-methylpentanoyl]-2,3-dihydro-1H-indol-3-yl)methyl]-quinazolino(3,2-A)-1,4-benzodiazepin-5,13-(5H,7H)-dione (isomer 1) and 7-[(1-[2(S)-((1,1-dimethylethoxy)carbonyl)amino-4-methylpentanoyl]-2,3-dihydro-1H-indol-3-yl)methyl]quinazolino(3,2-A)-1,4-benzodiazepin-5,13-(6H,7H)-dione.

The pharmaceutically-acceptable salts of the compounds of the instant invention include the conventional soluble, non-toxic salts of the compounds of this invention formed, for example, from non-toxic inorganic or organic acids. Such conventional non-toxic salts include those derived from inorganic acids, such as hydrochloric, hydrobromic, sulfuric, sulfamic, phosphoric, nitric and the like; or organic acids, such as acetic, trifluoroacetic, propionic, succinic, stearic, lactic, malic, tartaric, citric, benzoic, toluenesulfonic, methanesulfonic, ethane disulfonic, oxalic, isethionic, and the like.

Compounds according to formula II of the instant invention and salts thereof may be produced by three schemes, viz:

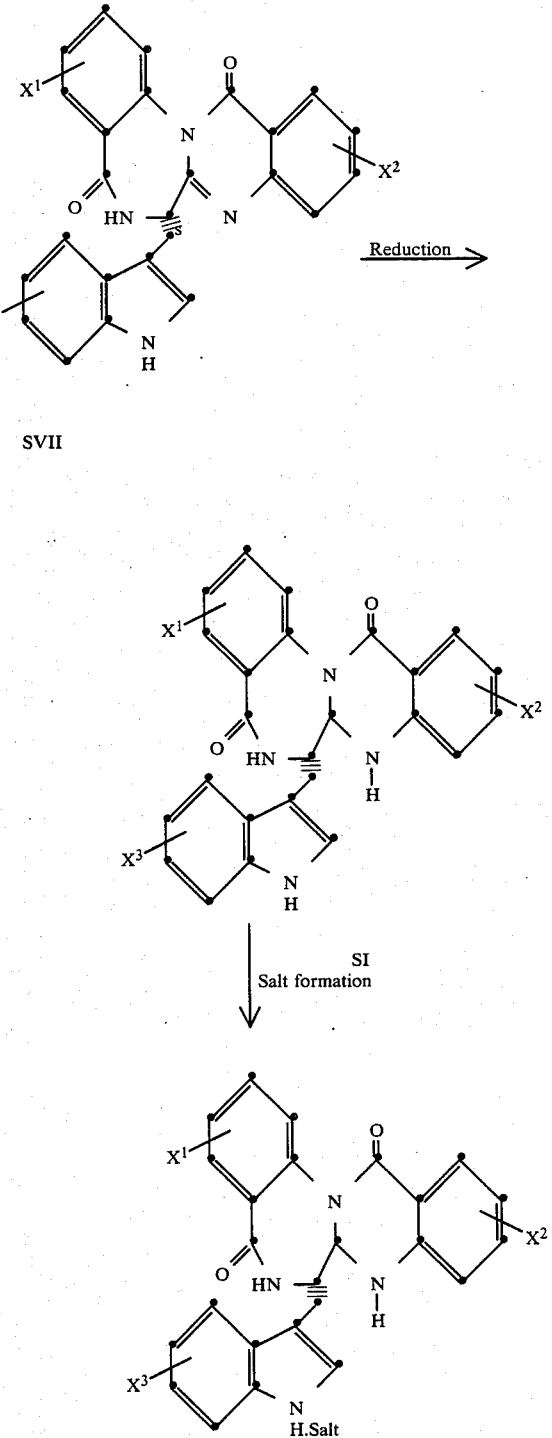

SCHEME II
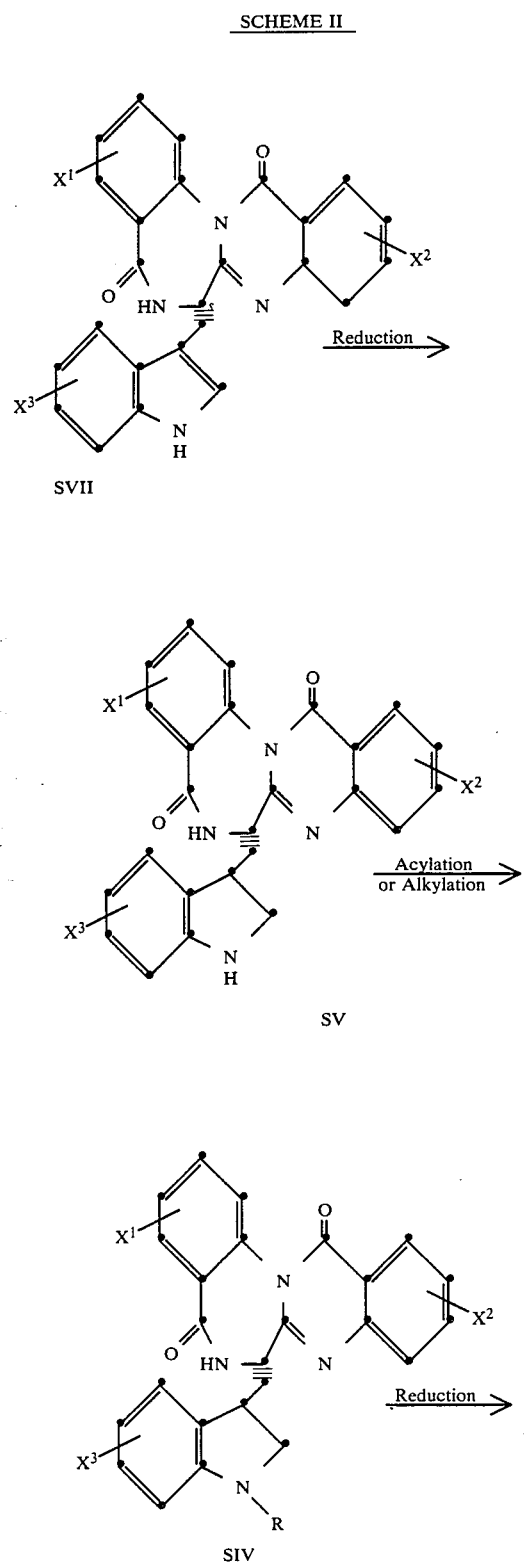
SCHEME II -continued
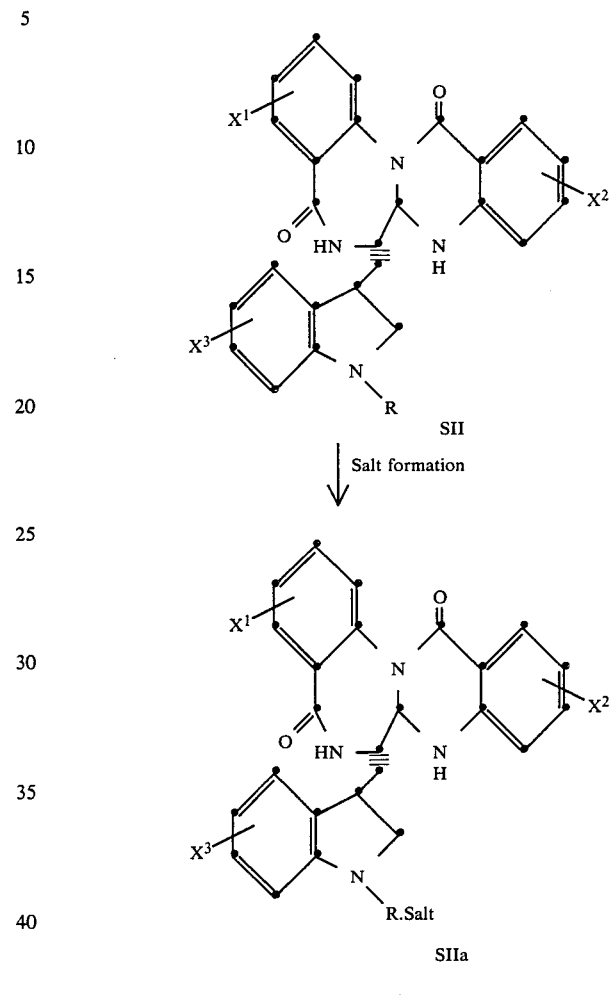
SCHEME III
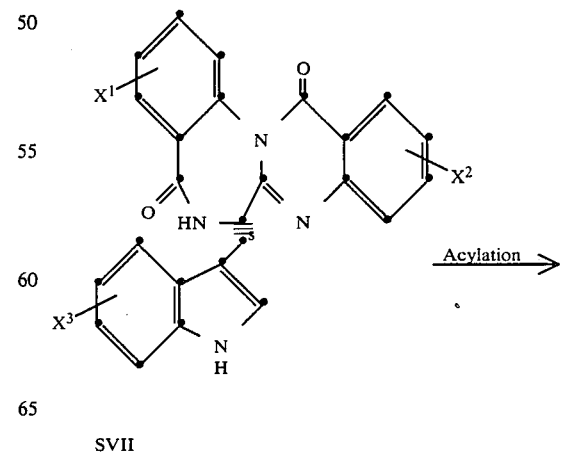

-continued
SCHEME III

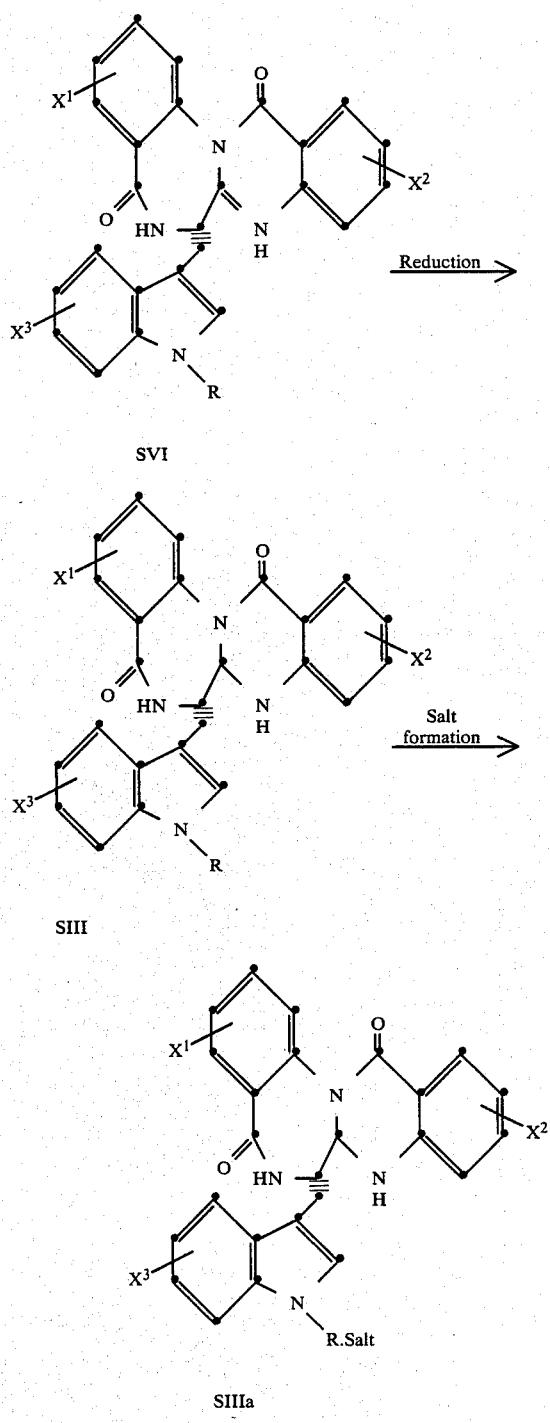

According to Scheme I, compounds of the general formula SI may be obtained by reducing compounds of the general formula SVII by reacting a compound of formula SVII in a protic solvent, such as water, acetic acid, trifluoroacetic acid, methanol, ethanol and the like, or in an aprotic solvent, such as tetrahydrofuran, with a reducing agent, such as sodium cyanoborohydride or lithium, sodium, or potassium borohydride, in a suitable medium, such as acetic acid, trifluoroacetic acid or ethanol, at from −40° C. to the boiling point of the solvent, for from 5 minutes to 10 hours. Preferably, the reaction is carried out in an acidic medium, such as acetic acid or trifluoroacetic acid, at 15° C. for 0.5 hours with sodium cyanoborohydride.

Compounds of the general formula SI may then subsequently be converted to their corresponding salts of formula SIa. This may be accomplished by conventional chemical means by suspending compounds of formula SI in a solvent, such as water, methanol, ethanol, ethyl acetate, tetrahydrofuran, or other suitable organic solvent or combinations of solvents, and treating the resulting reaction mixture with stoichiometric amounts of or with an excess of the desired salt-forming inorganic or organic acid. Examples of appropriate inorganic acids for conversion of the compounds of formula SI to the corresponding salts include mineral acids, such as hydrochloric and hydrobromic acids, while appropriate organic acids include trifluoroacetic, ethane disulfonic, or isethionic acids, and the like.

According to Scheme II, compounds of the general formula SV may be obtained by reacting a compound of formula SVII in an acidic medium, preferably trifluoroacetic acid, at from −20° C. to the boiling point of the medium, with a suitable hydride reducing agent, such as sodium cyanoborohydride, triethylsilane or trimethylsilane. Preferably, the reaction is carried out at room temperature with triethylsilane for 10 hours. These reduced compounds of formula SV may subsequently be acylated with an electrophilic acylating agent, such as the carbonic acids, 2(S)-(1,1-dimethylethoxycarbonyl)amino-4-methylpentanoic acid or 2-(benzyloxycarbonyl)amino-4-methylpentanoic acid in an inert, aprotic solvent, such as N,N-dimethylformamide, acetonitrile, dimethylsulfoxide, chloroform, methylene chloride, tetrahydrofuran, dioxane, toluene, and chlorobenzene, at temperatures of from −30° C. to the boiling point of the solvent, preferably at room temperature, in the presence of suitable coupling reagent, such as dicyclohexylcarbodiimide, 1-ethyl-3-(3-dimethylaminopropyl)carbodiimide hydrochloride, carbonyldiimidazole, or the like. If a carbonic acid anhydride, such as acetic anhydride, or a carbonic acid halogenate, such as acetyl chloride or benzylchloroformate, is used as electrophilic acylating agent, then the reaction is preferably carried out in the presence of an acid binding agent, such as a tertiary amine, including triethylamine, pyridine, 4-dimethylaminopyridine and the like, or an alkali metal hydroxide or alkali metal carbonate, including sodium hydroxide, potassium carbonate, and the like, in an aprotic solvent at temperatures of from −30° C. to the boiling point of the solvent with the exclusion of moisture.

Additionally, compounds of the general formula SV may be reacted with a suitable electrophilic alkylating agent, like an alkyl halide or an alkyl phenyl sulfonate, such as iodomethane, cyclohexyl iodide or butyl-p-toluenesulfonate, or the like, in a suitable solvent such as tetrahydrofuran, dimethyl sulfoxide, dimethylformamide, and the like, in the presence of a suitable base, such as triethylamine, pyridine, 4-dimethylaminopyridine, diisopropylethylamine, sodium hydroxide, potassium carbonate, and the like, to give compounds of the general formula SIV. These reactions may be carried out at from −30° C. to the boiling point of the solvent, preferably at room temperature, of from one to forty-eight hours.

Compounds of the general formula SII may then be obtained by reducing compounds of the general formula SIV by reacting a compound of formula SIV in aprotic solvent, such as water, methanol, ethanol, acetic acid, trifluoroacetic acid, and the like, or in an aprotic solvent, like tetrahydrofuran, with a reducing agent, such as sodium cyanoborohydride or lithium, sodium, or potassium borohydride, in a suitable medium, such as acetic acid, trifluoroacetic acid or ethanol, at from −40° to the boiling point of the solvent, for from 5 minutes to 10 hours. Preferably, the reaction is carried out in acetic acid or trifluoroacetic acid at 15° C. for 0.5 hours with sodium cyanoborohydride.

Compounds of general formula SII may then subsequently be converted to their corresponding salts (SIIa) using methodology described for the preparation of SIa compounds.

According to Scheme III, compound of the general formula SVI may be prepared by acylating compounds of the general formula SVII in an aprotic solvent or solvents, such as acetonitrile-dimethylformamide, at temperatures of from −30° C. to the boiling point of the solvent medium using, as an electrophilic acylating agent, an activated ester of a carboxylic acid, such as p-nitrophenyl-2(S)-(1,1-dimethylethoxycarbonyl-)amino-4-methylpentanoate, or p-nitrophenyl-2(S)-(benzyloxycarbonyl)amino-4-methylpentanoate, in the presence of a tertiary amine, such as triethylamine, diisopropylethylamine or trimethylamine, an alkali earth salt, such as lithium chloride, sodium chloride, or potassium fluoride and an alkali metal ion binding agent, such as 18-crown-6,15-crown-5,12-crown-4,dibenzo-18-crown-6, and the like. Preferably, the reaction is carried out at room temperature in acetonitrile-dimethylformamide with the exclusion of moisture using potassium fluoride, 18-crown-6 and diisopropylethylamine, p-nitrophenyl-2(S)-(1,1-dimethylethoxycarbonyl)amino-4-methylpentanoate or p-nitrophenyl-2(S)-(benzyloxycarbonyl)amino-4-methylpenatanoate. Compounds of the general formula SIII may then be obtained by reducing compounds of the general formula SVI by reacting a compound of formula SVI in a protic solvent, such as water, acetic acid, trifluoroacetic acid, methanol, ethanol, and the like, or in an aprotic solvent, like tetrahydrofuran, with a reducing agent, such as sodium cyanoborohydride or lithium, sodium, or potassium borohydride, in a suitable medium, such as acetic acid, trifluoroacetic acid or ethanol, at from −40° C. to the boiling point of the solvent, for from 5 minutes to 10 hours. Preferably, the reaction is carried out in an acidic medium, such as acetic acid or trifluoroacetic acid, at 15° C. for 0.5 hours with sodium cyanoborohydride.

Compounds of the general formula SIII may then subsequently be converted to their corresponding salts of formula SIIIa using methodology described for the preparation of SIa compounds.

Chiral acylating and alkylating agents of both configurations may be used for the production of analogs of the compounds according to the instant invention. The preferred stereochemical configuration of the products according to the instant invention, however, are those defined in Formula II.

Screening of the novel compounds according to the present invention to determine biological activity and obtain an $IC_{50}$ value for them, in order to identify significant CCK-antagonism, may be accomplished using an $^{125}I$-CCK receptor binding assay and in vitro isolated tissue preparations. These tests involve the following:

CCK receptor binding (pancreas) method

CCK-33 is radiolabeled with $^{125}I$-Bolton Hunter reagent (2000 Ci/mmole), as described by Sankara et al. (J. Biol. Chem., 254, 9349–9351, 1979). Receptor binding is performed according to Innis and Snyder (Proc. Natl. Acad. Sci., 77, 6917–6921, 1980), with the minor modification of adding the additional protease inhibitors, phenyl-methane sulfonyl fluoride and o-phenanthroline, which have no effect on the $^{125}I$-CCK receptor binding assay.

The whole pancreas of a male Sprague-Dawley rat (200–350 g), which has been sacrificed by decapitation, is dissected free of fat tissue and homogenized in 20 volumes of ice-cold 50 mM Tris HCl (pH 7.7 at 25° C.) with a Brinkman Polytron PT-10. The homogenates are centrifuged at 48,000 g for 10 minutes, then the resulting pellets are resuspended in Tris Buffer, centrifuged as above, and resuspended in 200 volumes of binding assay buffer (50 mM Tris HCl, pH 7.7 at 25° C., 5 mM dithiothreitol, 0.1 mM bacitracin, 1.2 mM phenylmethane sulfonyl fluoride and 0.5 mM o-phenanthroline).

For the binding assay, 25 µl of buffer (for total binding), or unlabeled CCK-8 sulfate sufficient to give a final concentration of 1 µM of CCK-8 (for nonspecific binding), or the compounds of the formula of the compounds according to the instant invention (for determination of antagonism to $^{125}I$-CCK binding) and 25 µl of $^{125}I$-CCK-33 (30,000–40,000 cpm), are added to 450 µl of the membrane suspensions in microfuge tubes. All assays are run in duplicate or triplicate, and the reaction mixtures are incubated at 37° C. for 30 minutes and centrifuged in a Beckman Microfuge (4 minutes) immediately after adding 1 ml of ice-cold incubation buffer. The supernatant is aspirated and discarded, and the pellets are counted with a Beckman Gamma 5000. For Scatchard analysis to determine the mechanism of inhibition of $^{125}I$-CCK binding by the most potent compounds (Ann. N.Y. Acad. Sci., 51, 660, 1949), $^{125}I$-CCK-33 is progressively diluted with increasing concentrations of CCK-33.

CCK receptor binding (brain) method

CCK-33 is radiolabeled and the binding is performed according to the description for the pancreas method, with modifications according to Saito et al., J. Neurochem., 37, 483–490, 1981.

Male Hartley guinea pigs (300–500 g) are sacrificed by decapitation, and the brains are removed and placed in ice-cold 50 mM Tris HCl (Trizma-7.4) [pH 7.4 at 25° C.]. The cerebral cortex is dissected and used as a receptor source and each gram of fresh guinea pig brain tissue is homogenized in 10 ml of Tris/Trizma buffer with a Brinkman polytron PT-10. The homogenates are centrifuged at 42,000 g for 15 minutes, then the resulting pellets are resuspended in 80 volumes of binding assay buffer (10 mM N-2-hydroxy-ethylpiperazine-N'-2-ethanesulfonic acid (HEPES), 5 mM $MgCl_2$, 1 mM ethylene glycol-bis-(β-amino-ethyl-ether-N,N'-tetraacetic acid (EGTA), 0.4% BSA and 0.25 mg/ml bacitracin, pH 6.5).

The remainder of the binding assay method is as described for the pancreas method, except that the reaction mixtures are incubated at 25° C. for 2 hours before centrifugation.

An additional method of confirming competitive antagonism of CCK which may be used is the following:

Isolated guinea pig gall bladder method

The two halves of the gall bladders, free of adjacent tissue, of male Hartley guinea pigs (400-600 g), which have been sacrificed by decapitation, are suspended under 1 g tension along the axis of the bile duct in 5 ml organ bath, containing a Kreb's bicarbonate solution of 118 mM NaCl, 4.75 mM KCl, 2.54 $CaCl_2$, 1.19 mM $KH_2PO_4$, 1.2 mM $MgSO_4$, 25 mM $NaHCO_3$ and 11 mM dextrose, which is maintained at 32° C. and bubbled with a mixture of 95% $O_2$ and 5% $CO_2$. The tissues are washed every 10 minutes for 1 hour to obtain equilibrium prior to the beginning of the study and the isometric contractions of the strips are recorded using Statham (60 g:0.12 mm) strain gauges and a Hewlett-Packard 77588 recorder.

CCK-8 is added cumulatively to the baths and $EC_{50}$'s are determined using regression analysis. After washout (every 10 minutes for 1 hour), the compound to be tested is added at least 5 minutes before the addition of CCK-8 and the $EC_{50}$ of CCK-8 in the presence of compound to be tested is similarly determined.

A shift to the right of the CCK dose response curve without reduction of the maximal contractile response, indicates competitive antagonism of CCK from this method.

The ability of the compounds of the instant invention to antagonize CCK makes these compounds useful as pharmaceutical agents for mammals, especially for humans, for the treatment and prevention of disorders wherein CCK may be involved. Examples of such disease states include gastrointestinal disorders, especially such as irritable bowel syndrome or ulcers, excess pancreatic or gastric secretion, acute pancreatis, or motility disorders; central nervous system disorders, caused by CCK interactions with dopamine, such as neuroleptic disorders, tardive dyskinesia, Parkinson's disease, psychosis or Gilles de la Tourette Syndrome; and disorders of appetite regulatory systems.

The compounds of the instant invention or pharmaceutically-acceptable salts thereof, may be administered to a human subject either alone or, preferably, in combination with pharmaceutically-acceptable carriers or diluents, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramusclar, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to the instant invention, or a salt thereof, is used as an antagonist of CCK in a human subject, the daily dosage will normally be determined by the prescribing physician. Moreover, the dosage will vary according to the age, weight, and response of the individual patient, as well as the severity of the patient's symptoms. In most instances, an effective daily dosage will be in the range of from about 1 mg to about 1500 mg, and preferably, of from 10 mg to about 500 mg administered in single or divided doses. In some cases, however, it may be necessary to use dosages outside these limits.

The invention is further defined by reference to the following examples which are intended to be illustrative and not limiting.

EXAMPLE 1

Preparation of 7,7A-dihydro-7-(1H-indol-3-yl)methylquinazolino(3,2-B)-1,4-benzodiazepin-5,13-(6H,9H)-dione monohydrate

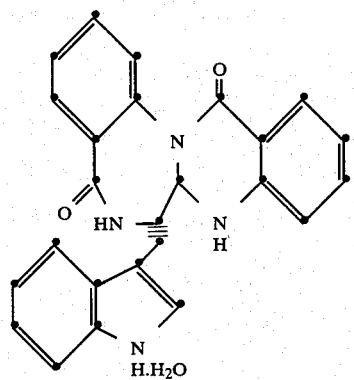

7-[(1H-Indol-3-yl)methyl]quinazolino(3,2-A)-1,4-benzodiazepin-5,13-(6H,7H)-dione (410 mg, 1.0 mmole) was suspended in 30 ml of glacial acetic acid at 10° C. and sodium cyanoborohydride (300 mg, 5.0 mmole) was added to this mixture. The reaction was stirred for 1 hour, warmed to room temperature and filtered. The filtrate was then diluted with 200 ml of water. The resulting precipitate was collected, washed with water, and dried to give 200 mg of a beige solid, m.p.. 175°(d).

PMR ($CD_3OD$): according to theory.

MS (FAB): 409 ($M^+ + H$), 249, 130.

Elemental Analysis for $C_{25}H_{20}N_4O_2 \cdot H_2O$ Calc'd: N, 13.14; C, 70.41; H, 5.20. Found: N, 13.71; C, 70.27; H, 5.08.

EXAMPLE 2

Preparation of 7-[(2,3-dihydro-1H-indol-3-yl)methyl]-quinazolino(3,2-A)-1,4-benzodiazepin-5,13-(6H,7H)-dione hemihydrate

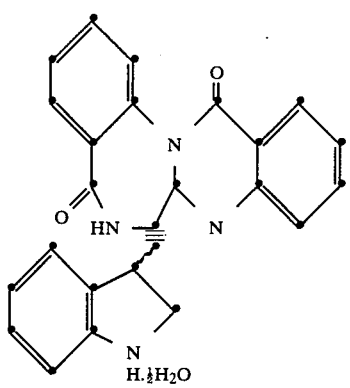

7-[(1H-Indol-3-yl)methyl]quinazolino(3,2-A)-1,4-benzodiazepin-5,13-(6H,7H)-dione (250 mg, 0.61 mmole) was dissolved in 2 ml of trifluoroacetic acid and treated in one portion with 106 μl (0.67 mmole) of triethylsilane under nitrogen. After 1 hour, 1 mmole more of triethylsilane was added and rapid stirring was continued overnight. Solvent and excess reagent were removed under reduced pressure and the residue partitioned between ethyl acetate and saturated sodium bicarbonate solution. The organic phase was washed with sodium bicarbonate solution and brine, then dried and concentrated. The resulting residue was purified by thick layer silica gel chromatography (9:1 ethyl acetate-hexane v/v) to give a white solid (yield 210 mg) as a mixture of diastereomers (approximately 58:42 HPLC). PMR (360 MHz, CD$_3$OD): spectrum confirms structure assignment.

Elemental Analysis for C$_{25}$H$_{20}$N$_4$O$_2$.½H$_2$O Calc'd: N, 13.42; C, 71.92; H, 5.07. Found: N, 12.99; C, 71.85; H, 5.20.

EXAMPLE 3

Preparation of 7-[(1-[2(S)-((1,1-dimethylethoxy)-carbonyl)amino-4-methylpentanoyl]-1H-indol-3-yl)methyl]-quinazolino(3,2-A)-1,4-benzodiazepin-5,13-(6H,7H)-dione sesquihydrate

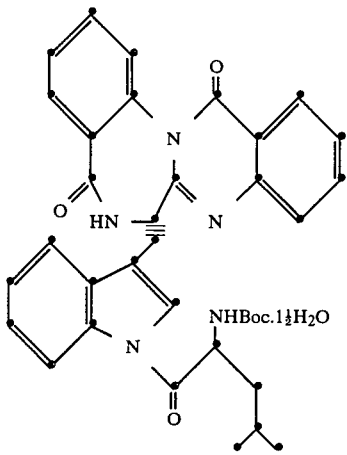

Potassium fluoride (117 mg, 2.02 mmole) was added to 10 ml of dry acetonitrile containing 1,4,7,10,13,16-hexaoxacyclooctadecane (266 mg, 1.01 mmole). To this solution were added 7-[(1H-indol-3-yl)methyl]-quinazolino-(3,2-A)-1,4-benzodiazepin-5,13-(6H,7H)-dione (492 mg, 1.01 mmole), p-nitrophenyl-2(S)-((1,1-dimethyl)ethoxycarbonyl)amino-4-methylpentanoate (441 mg, 1.25 mmole) and 218 μl (1.25 mmole) of diisopropylethylamine under nitrogen. The reaction mixture was stirred rapidly, 10 ml of dimethylformamide was added, and one equivalent of each of the above reagents was added. After 60 hours, the reaction mixture was partitioned between ethyl acetate and water; the phases were separated and the organic layer was washed in succession with saturated sodium bicarbonate solution, 10% citric acid solution, and brine. Rotoevaporation of the dried (MgSO$_4$) extracts gave a solid which was purified by silica gel chromatography (1:1 hexaneethyl acetate v/v).

MS (FAB): 620 (M$^+$+H), 642 (M$^+$+Na), 564, 407.

PMR (CDCl$_3$): according to theory.

Elemental analysis for C$_{36}$H$_{37}$N$_5$O$_5$.1.5H$_2$O Calc'd: N, 10.83; C, 66.86; H, 6.23. Found: N, 10.67; C, 66.91; H, 6.37.

EXAMPLE 4

Preparation of
7-[(1-[2(S)-((1,1-dimethylethoxy)carbonyl)amino-4-methylpentanoyl]-2,3-dihydro-1H-indol-3-yl)methyl]-quinazolino(3,2-A)-1,4-benzodiazepin-5,13-(6H,7H)-dione hemihydrate

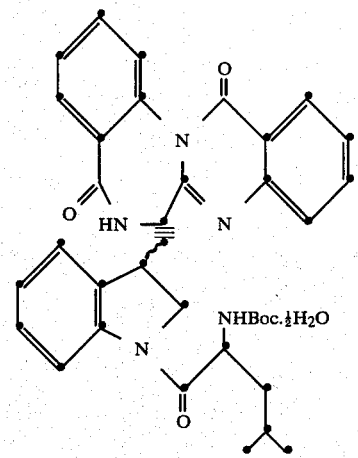

7-[(2,3-Dihydro-1H-indol-3-yl)methyl]-quinazolino(3,2-A)-1,4-benzodiazepin-5,13-(6H,7H)-dione (50 mg, 0.122 mmole) was dissolved in 2 ml of dry dimethylformamide under nitrogen and treated at room temperature with 2-(S)-(1,1-dimethylethoxycarbonyl)amino-4-methylpentanoic acid (34 mg, 0.146 mmole), 1-hydroxybenzotriazole (20 mg, 0.146 mmole), and dicyclohexylcarbodiimide (30 mg, 0.146 mmole), respectively. The pH of the reaction mixture was adjusted to approximately 8 with triethylamine (20 μl) and the reaction was stirred at room temperature overnight. The solvent was removed under reduced pressure and the residue was partitioned between ethyl acetate and saturated sodium bicarbonate solution. The organic phase was washed with 10% citric acid and brine, then dried and concentrated. Silica gel chromatography (95:5 chloroform-methanol) afforded 23 mg of the analytical sample along with 19 mg recovered starting material.

MS (FAB): 622 (M++H), 522, 409, 317.

PMR (CDCl$_3$): confirms structure.

Elemental analysis for $C_{36}H_{39}N_5O_5 \cdot \frac{1}{2}H_2O$ Calc'd: N, 11.12; C, 68.66; H, 6.40. Found: N, 11.12; C, 68.81; H, 6.54.

EXAMPLE 5

Preparation of
7-[(1-[2(S)-((1,1-dimethylethoxy)carbonyl)amino-4-methylpentanoyl]-2,3-dihydro-1H-indol-3-yl)methyl]-quinazolino(3,2-A)-1,4-benzodiazepin-5,13-(5H,7H)-dione hydrate

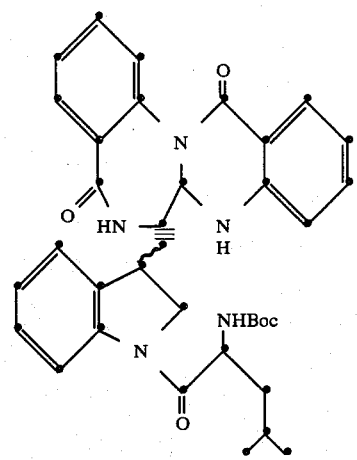

7-[(1-[2(S)-((1,1-Dimethylethoxy)carbonyl)amino-4-methylpentanoyl]-2,3-dihydro-1H-indol-3-yl)-methyl]-quinazolino(3,2-A)-1,4-benzodiazepin-5,13-(6H,7H)-dione (250 mg, 0.40 mmole) was dissolved in 4 ml of glacial acetic acid and treated at 10° with 101 mg (1.60 mmole) of sodium cyanoborohydride. After twenty minutes, the reaction mixture was poured into 50 ml of water and then extracted with ethyl acetate (4×40 ml). The combined organic extracts were washed with saturated sodium bicarbonate solution and brine, then dried (MgSO$_4$) and concentrated. The crude product was purified by preparative thick layer chromatography on silica gel (97:3 chloroform-methanol elution) to give the analytical sample as a mixture of diastereomers.

MS (FAB): 624 (M++H), 524, 369, 292, 249.

PMR (CDCl$_3$): according to theory.

Elemental analysis for $C_{36}H_{41}N_5O_5$ 0.6H$_2$O Calc'd: N, 11.03; C, 68.14; H, 6.70. Found: N, 10.87; C, 68.21; H, 6.94.

EXAMPLE 6

Preparation of
7-[(1-[2(R)-((1,1-dimethylethoxy)carbonyl)amino-4-methylpentanoyl]-2,3-dihydro-1H-indol-3-yl)methyl]-quinazolino(3,2-A)-1,4-benzodiazepin-5,13-(6H,7H)-dione hydrate, Isomer 1.

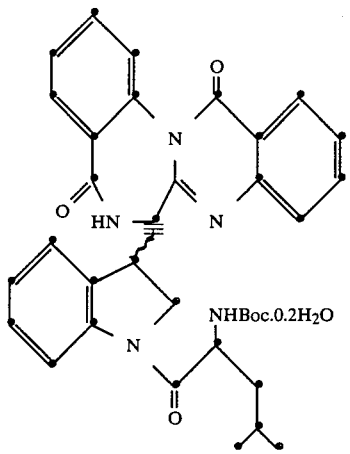

7-[(2,3-Dihydro-1H-indol-3-yl)methyl]-quinazolino(3,2-A)-1,4-benzodiazepin-5,13-(6H,7H)-dione (250 mg, 0.612 mmole), 2(R)-((1,1-dimethylethoxy)carbonyl)amino-4-methylpentanoic acid (142 mg, 0.734 mmole), 1-ethyl-3-dimethylaminopropylcarbodiimide hydrochloride (141 mg, 0.734 mmole), 1-hydroxybenzotriazole (99 mg, 0.734 mmole), and triethylamine (102 μl, 0.734 mmole) were mixed with 12 ml of dry dimethylformamide and the resulting mixture was protected from moisture and stirred at room temperature for 48 hours. The mixture was filtered, rotoevaporated and the residue partitioned between ethyl acetate and water. The organic phase was washed with saturated sodium bicarbonate solution, 10% citric acid and brine, then dried (MgSO₄) and concentrated. The crude product thus obtained as a mixture of diastereomers was purified by preparative thick layer chromatography (silica gel, 97:3 hexane-ethyl acetate v/v) to afford isomer 1. HPLC shows isomer 1 to be 78% diastereomerically pure.

MS (FAB): 622 (M++H), 522.

PMR (CDCl₃): according to theory.

Elementary analysis for $C_{36}H_{39}N_5O_5 \cdot 0.2H_2O$ Calc'd: N, 11.20; C, 69.14; H, 6.35. Found: N, 11.30; C, 68.95; H, 6.38.

EXAMPLE 7

Preparation of
7-[(1-[2(R)-((1,1-dimethylethoxy)carbonyl)amino-4-methylpentanoyl]-2,3-dihydro-1H-indol-3-yl)methyl]-quinazolino(3,2-A)-1,4-benzodiazepin-5,13-(6H,7H)-dione hydrate, Isomer 2

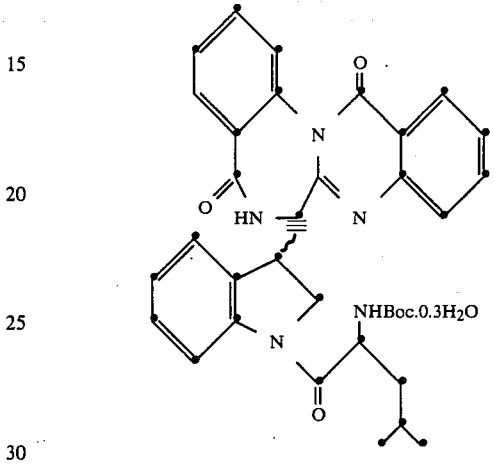

7-[(2,3-Dihydro-1H-indol-3-yl)methyl]-quinazolino(3,2-A)-1,4-benzodiazepin-5,13-(6H,7H)-dione (250 mg, 0.612 mmole), 2(R)-((1,1-dimethylethoxy)carbonyl)amino-4-methylpentanoic acid (142 mg, 0.734 mmole), 1-ethyl-3-(3-dimethylaminopropyl)carbodiimide hydrochloride (141 mg, 0.734 mmole), 1-hydroxybenzotriazole (99 mg, 0.734 mmole), and triethylamine (102 μl, 0.734 mmole) were mixed with 12 ml of dry dimethylformamide and the resulting mixture was protected from moisture and stirred at room temperature for 48 hours. The mixture was filtered, rotoevaporated and the residue partitioned between ethyl acetate and water. The organic phase was washed with saturated sodium bicarbonate solution, 10% citric acid and brine, then dried (MgSO₄) and concentrated. The crude product thus obtained as a mixture of diastereomers was purified by preparative thick layer chromatography (silica gel, 97:3 hexane-ethyl acetate v/v) to afford isomer 2.

HPLC shows isomer 2 to be 92% diastereomericaly pure.

MS (FAB): 622 (M++H), 522, 409.

PMR (CDCl₃): according to theory.

Elemental analysis for $C_{36}H_{39}N_5O_5 \cdot 0.3H_2O$ Calc'd: N, 11.16; C, 68.94; H, 6.36. Found: N, 11.07; C, 69.02; H, 6.53.

EXAMPLE 8

Preparation of
7-[(1-[2(R)-((1,1-dimethylethoxy)carbonyl)amino-4-methylpentanoyl]-2,3-dihydro-1H-indol-3-yl)methyl]-quinazolino(3,2-A)-1,4-benzodiazepin-5,13-(5H,7H)-dione hydrate, Isomer 1

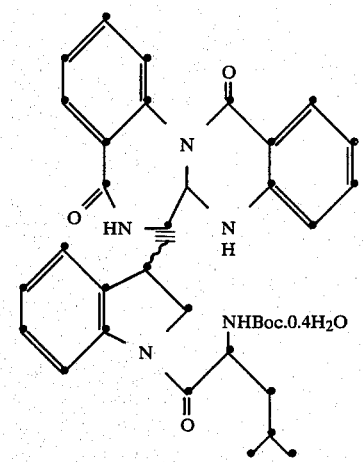

NHBoc.0.4H$_2$O

7-[(1-[2(R)-((1,1-Dimethylethoxy)carbonyl)amino-4-methylpentanoyl]-2,3-dihydro-1H-indol-3-yl)methyl]-quinazolino(3,2-A)-1,4-benzodiazepin-5,13-(6H,7H)-dione (120 mg, 0.19 mmole) was dissolved in 3 ml of glacial acetic acid and treated at 10° with 48 mg (0.77 mmole) of sodium cyanoborohydride. After twenty minutes, the reaction mixture was poured into 50 ml of water, extracted with ethyl acetate (4×40 ml) and the combined organic extracts were washed with saturated sodium bicarbonate solution and brine, then dried (MgSO$_4$) and concentrated. The crude product was purified by preparative thick layer chromatography on silica gel (98:2 chloroform-methanol, multiple elutions) to give the analytical product as isomer 1, the faster eluting component.

MS (FAB): 624 (M$^+$ +H), 524, 292 (Base peak).

PMR (CDCl$_3$): according to theory.

Elemental analysis for C$_{36}$H$_{41}$N$_5$O$_5$.0.4H$_2$O Calc'd: N, 11.10; C, 68.53; H, 6.67. Found: N, 10.89; C, 68.64; H, 6.85.

EXAMPLE 9

Preparation of
7-[[1-[2(R)-((1,1-dimethylethoxy)carbonyl)amino-4-methylpentanoyl]-2,3-dihydro-1H-indol-3-yl)methyl]-quinazolino(3,2-A)-1,4-benzodiazepin-5,13-(5H,7H)-dione hydrate, Isomer 2

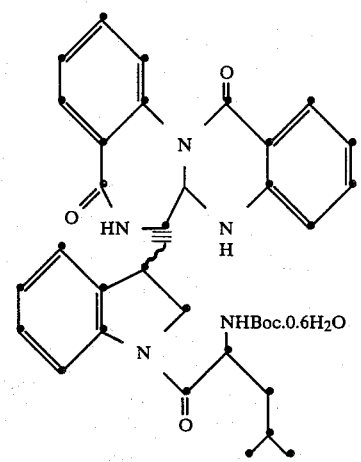

NHBoc.0.6H$_2$O

7-[(1-[2(R)-((1,1-dimethylethoxy)carbonyl)amino-4-methylpentanoyl]-2,3-dihydro-1H-indol-3-yl)methyl]-quinazolino(3,2-A)-1,4-benzodiazepin-5,13-(6H,7H)-dione (120 mg, 0.19 mmole) was dissolved in 3 ml of glacial acetic acid and treated at 10° with 48 mg (0.77 mmole) of sodium cyanoborohydride. After twenty minutes, the reaction mixture was poured into 50 ml of water, extracted with ethyl acetate (4×40 ml) and the combined organic extracts were washed with saturated sodium bicarbonate solution and brine, then dried (MgSO$_4$) and concentrated. The crude product was purified by preparative thick layer chromatography on silica gel (98:2 chloroform-methanol, multiple elutions) to give the analytical product as isomer 2, the slower eluting component.

MS (FAB): 624 (M$^+$ +H), 524, 292 (Base peak).

PMR (CDCl$_3$): according to theory.

Elemental analysis for C$_{36}$H$_{41}$N$_5$O$_5$.H$_2$O Calc'd: N, 11.03; C, 68.14; H, 6.70. Found: N, 10.69; C, 68.17; H, 6.62.

EXAMPLE 10

Preparation of 7-[(1-[2(S)-phenylmethoxycarbonylamino-4-methylpentanoyl]-1H-indol-3-yl)methyl]quinazolino-(3,2-B)-1,4-benzodiazepin-5,13-(6H,7H)-dione

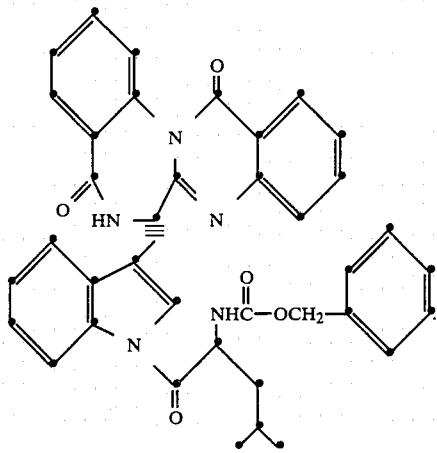

Potassium fluoride (371 mg, 6.39 mmole) was added to 10 ml of dry acetonitrile containing 1,4,7,10,13,16-hexaoxacyclooctadecane (845 mg, 3.19 mmole) and 7-[(1H-indol-3-yl)methyl]quinazolino-(3,2-A)-1,4-benzodiazepin-5,13-(6H,7H)-dione (848 mg, 2.00 mmole), p-nitrophenyl 2(S)-phenylmethoxycarbonylamino-4-methylpentanoate (811 mg, 2.10 mmole) and 0.37 ml (2.10 mmole) of diisopropylethylamine were added to this solution, under nitrogen. The reaction mixture was stirred rapidly, 20 ml of dimethylformamide was added, and one equivalent each of the above reagents was added. After 60 hours, the reaction mixture was partitioned between ethyl acetate and water; the phases were separated and the organic layer was washed in succession with saturated sodium bicarbonate solution, 10% citric acid solution, and brine. Rotoevaporation of the dried (MgSO$_4$) extracts gave a solid which was purified by silica gel chromatography (1:1 hexane-ethyl acetate) to give 0.5 g of the analytical product as a beige powder.

MS (FAB): 654 (M$^+$+H), 502, 500.

PMR (CDCl$_3$): according to theory.

Elemental analysis for C$_{39}$H$_{35}$N$_5$O$_5$ Calc'd: N, 10.71; C, 71.65; H, 5.39. Found: N, 10.55; C, 71.65; H, 5.88.

EXAMPLE 11

Activity Testing

The compounds of Examples 1–10 were tested as CCK-antagonists with the following results:

| Compound from Example | X$^1$ | X$^2$ | X$^3$ | Substituents R | 2,3-Indole Bond | 7A-8 Bond | I-CCK-8 Pancreas IC$_{50}$ ($\mu$M) | $^{125}$I-CCK Brain IC$_{50}$ ($\mu$M) |
|---|---|---|---|---|---|---|---|---|
| 1 | H | H | H | H | Unsaturated | Saturated | 12 | >100 |
| 2 | H | H | H | H | Saturated | Unsaturated | 27 | >100 |
| 3 | H | H | H | —C(=O)—CH(NHBoc)—CH$_2$CH(CH$_3$)$_2$ | Unsaturated | Unsaturated | >100 | >100 |
| 4 | H | H | H | —C(=O)—CH(NHBoc)—CH$_2$—CH(CH$_3$)$_2$ | Saturated | Unsaturated | 3.4 | >100 |
| 5 | H | H | H | —C(=O)—CH(NHBoc)—CH$_2$—CH(CH$_3$)$_2$ | Saturated | Saturated | 19.2 | >100 |
| 6 | H | H | H | —C(=O)—CH(NHBoc)—CH$_2$—CH(CH$_3$)$_2$ | Saturated | Unsaturated | 16.5$^a$ | >100 |
| 7 | H | H | H | —C(=O)—CH(NHBoc)—CH$_2$—CH(CH$_3$)$_2$ | Saturated | Unsaturated | >100$^b$ | >100 |
| 8 | H | H | H | —C(=O)—CH(NHBoc)—CH$_2$CH(CH$_3$)$_2$ | Saturated | Saturated | 49$^a$ | 15 |
| 9 | H | H | H | —C(=O)—CH(NHBoc)—CH$_2$CH(CH$_3$)$_2$ | Saturated | Saturated | 34$^b$ | 100 |

-continued

Activity Testing
The compounds of Examples 1–10 were tested as CCK-antagonists with the following results:

| Compound from Example | $X^1$ | $X^2$ | $X^3$ | Substituents R | 2,3-Indole Bond | 7A-8 Bond | I-CCK-8 Pancreas $IC_{50}$ (μM) | $^{125}$I-CCK Brain $IC_{50}$ (μM) |
|---|---|---|---|---|---|---|---|---|
| 10 | H | H | H | 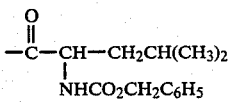 | Unsaturated | Unsaturated | >100 | >100 |

[a] Isomer 1.
[b] Isomer 2.

What is claimed is:

1. An indol-3-yl-quinazolino-1,4-benzodiazepin-5,13-dione of the formula:

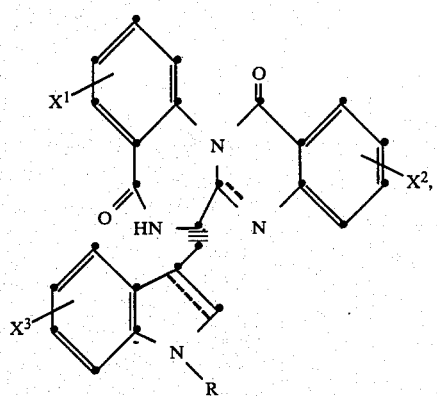

(II)

wherein:

$X^1$, $X^2$ and $X^3$ are independently H, Br, Cl, F, OH, $C_1$–$C_4$-alkyl, O—$C_1$–$C_4$-alkyl or

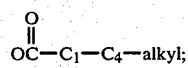

R is H; $C_1$–$C_8$-straight- or branched-chain alkyl; $C_3$–$C_8$-cyclic alkyl; $C_1$–$C_8$-straight- or branched-chain aralkyl, where the aryl is phenyl or naphthyl, which is unsubstituted or is monosubstituted on the aromatic ring by Br, Cl, F, OH, O—$C_1$–$C_4$-alkyl,

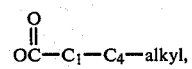

$C_1$–$C_4$-alkyl, $NO_2$, $NH_2$, CN or $CF_3$;

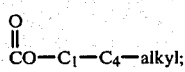

CO—$CH_2$—unsubstituted or monosubstituted phenyl or naphthyl, where the substituent is Br, Cl, F, OH, O—$C_1$–$C_4$-alkyl,

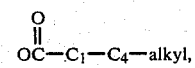

$NO_2$, CN, $C_1$–$C_4$-alkyl, or $CF_3$;

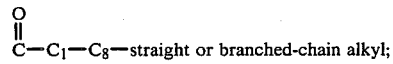

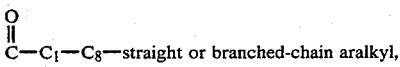

where the aryl is phenyl or naphthyl, which is unsubstituted or is monosubstituted on the aromatic ring by Br, Cl, F, OH, O—$C_1$–$C_4$-alkyl,

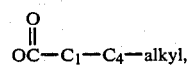

$C_1$–$C_4$-alkyl, $NO_2$, $NH_2$, CN or $CF_3$;

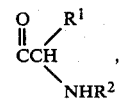

where $R^1$ is H; $C_1$–$C_4$-straight or branched-chain alkyl; $CH_2$-unsubstituted or monosubstituted phenyl, wherein the substituent is Br, Cl, F, OH, O—$C_1$–$C_4$-alkyl, O—$CH_2$-phenyl, or

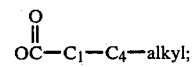

$CH_2$-3-indole; $CH_2$-imidazole; $CH_2CH_2SCH_3$;

hydroxy-$C_1$–$C_4$-alkyl; $(CH_2)_n NH_2$; or

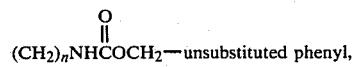

wherein n is 1 to 4; and $R^2$ is H,

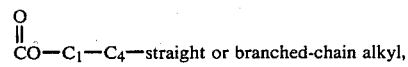

or

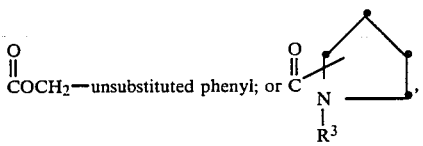

where R³ is H,

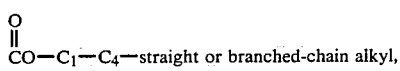

or

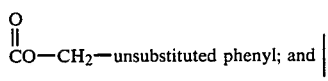

is a saturated (single) unsaturated (double) bond; or pharmaceutically-acceptable salts of these compounds.

2. A compound according to claim 1, wherein $X^1$, $X^2$ and $X^3$ are H; R is

where $R^1$ is $CH_2CH(CH_3)_2$ and $R^2$ is

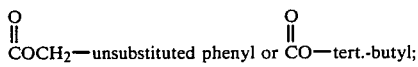

and the variable bonds are either both saturated or one is saturated and the other is unsaturated, and pharmaceutically-acceptable salts thereof.

3. A compound according to claim 1, wherein $X^1$, $X^2$ and $X^3$ are H; R is

where $R^1$ is $CH_2CH(CH_3)_2$ and $R^2$ is

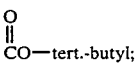

and the variable bonds are either both saturated or one is saturated and the other is unsaturated, and pharmaceutically-acceptable salts thereof.

4. A compound according to claim 1, selected from: 7,7A-dihydro-7-[(1H-indol-3-yl)methylquinazolino(3,2-B)-1,4-benzodiazepin-5,13-(6H,9H)-dione; 7-[(2,3-dihydro-1H-indol-3-yl)-methyl]quinazolino-(3,2-A)-1,4-benzodiazepin-5,13-(6H,7H)-dione; 7-[(1-[2(S)-((1,1-dimethylethoxy)carbonyl)amino-4-methylpentanoyl]-1H-indol-3-yl)methyl]quinazolino(3,2-A)-1,4-benzodiazepin-5,13-(6H,7H)-dione; 7-[(1-[2(S)-((1,1-dimethylethoxy)carbonyl)amino-4-methylpentanoyl]-2,3-dihydro-1H-indol-3-yl)methyl]quinazolino(3,2-A)-1,4-benzodiazepin-5,13-(6H,7H)-dione; 7-[(1-[2(S)-((1,1-dimethylethoxy)carbonyl)amino-4-methylpentanoyl]-2,3-dihydro-1H-indol-3-yl]methyl]quinazolino(3,2-A)-1,4-benzodiazepin-5,13-(5H,7H)-dione; 7-[(1-[2(R)-((1,1-dimethylethoxy)carbonyl)amino-4-methylpentanoyl]-2,3-dihydro-1H-indol-3-yl)methyl]quinazolino(3,2-A)-1,4-benzodiazepin-5,13-(6H,7H)-dione; 7-[[1-[2(R)-((1,1-dimethylethoxy)carbonyl)amino-4-methylpentanoyl]-2,3-dihydro-1H-indol-3-yl]methyl]-quinazolino(3,2-A)-1,4-benzodiazepin-5,13-(5H,7H)-dione; and 7-[(1-[2(S)-phenylmethoxycarbonylamino-4-methylpentanoyl]-1H-indol-3-yl)methyl]quinazolino-(3,2-B)-1,4-benzodiazepin-5,13-(6H,7H)-dione.

5. A compound according to claim 1, selected from 7-[(1-[2(R)-((1,1-dimethylethoxy)carbonyl)amino-4-methylpentanoyl]-2,3-dihydro-1H-indol-3-yl)methyl]-quinazolino(3,2-A)-1,4-benzodiazepin-5,13-(5H,7H)-dione (isomer 1) and 7-[(1-[2(S)-((1,1-dimethylethoxy)carbonyl)amino-4-methylpentanoyl]-2,3-dihydro-1H-indol-3-yl)methyl]quinazdino(3,2-A)-1,4-benzodiazepin-5,13-(6H,7H)-dione.

6. A process for preparing an indol-3-yl-quinazolino-1,4-benzodiazepin-5,13-dione of formula II:

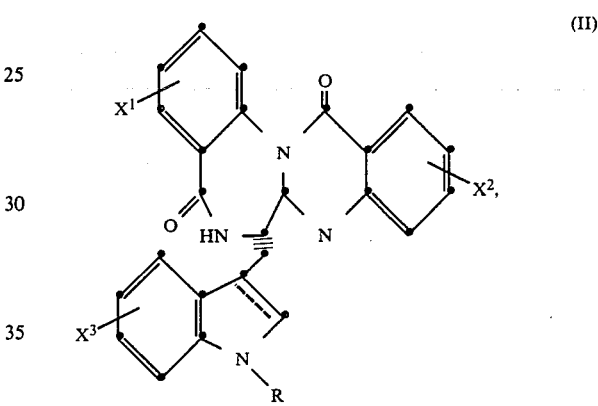

wherein:
$X^1$, $X^2$ and $X^3$ are independently H, Br, Cl, F, OH, $C_1$-$C_4$-alkyl, O—$C_1$-$C_4$-alkyl or

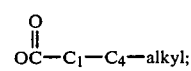

R is H; $C_1$-$C_8$-straight- or branched-chain alkyl; $C_3$-$C_8$-cyclic alkyl; $C_1$-$C_8$-straight- or branched-chain aralkyl, where the aryl is phenyl or naphthyl, which is unsubstituted or is monosubstituted on the aromatic ring by Br, Cl, F, OH, O—$C_1$-$C_4$-alkyl,

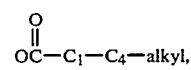

$C_1$-$C_4$-alkyl, $NO_2$, $NH_2$, CN or $CF_3$;

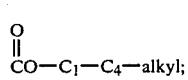
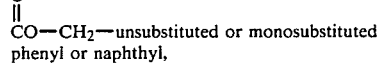

where the substituent is Br, Cl, F, OH, O—$C_1$-$C_4$-alkyl,

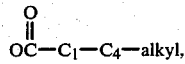

$C_1$–$C_4$-alkyl, $NO_2$, CN, or $CF_3$;

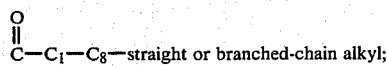

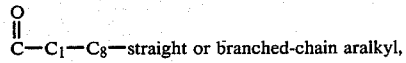

where the aryl is phenyl or naphthyl, which is unsubstituted or is monosubstituted on the aromatic ring by Br, Cl, F, OH, O—$C_1$-$C_4$-alkyl,

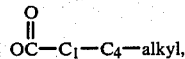

$C_1$–$C_4$-alkyl, $NO_2$, $NH_2$, CN or $CF_3$;

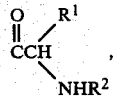

where $R^1$ is H; $C_1$–$C_4$-straight or branched-chain alkyl; $CH_2$-unsubstituted or monosubstituted phenyl, wherein the substituent is Br, Cl, F, OH, O—$C_1$–$C_4$-alkyl, O—$CH_2$-phenyl, or

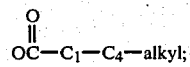

$CH_2$-3-indole; $CH_2$-imidazole; $CH_2CH_2SCH_3$;

hydroxy-$C_1$–$C_4$-alkyl; $(CH_2)_nNH_2$; or

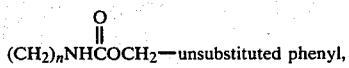

wherein n is 1 to 4; and $R^2$ is H,

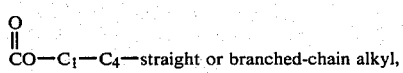

or

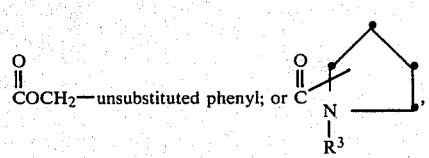

where $R^3$ is H,

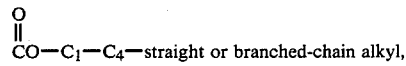

or

is a saturated (single) or unsaturated (double) bond; comprising reducing compounds of the formula (SVII):

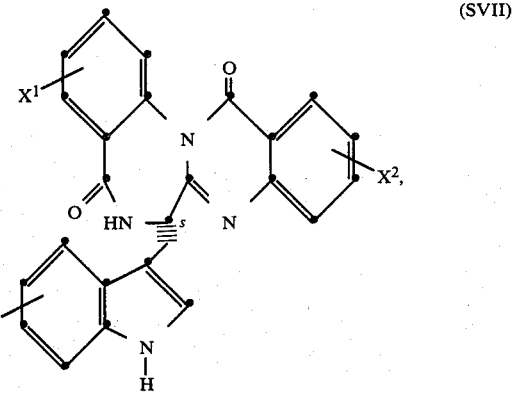

(SVII)

with a suitable reducing agent in a suitable acidic medium; or reducing compounds of formula SVII with a suitable reducing agent in a suitable acidic medium and acylating or alkylating these reduced compounds with an electrophilic acylating or electrophilic alkylating agent in a suitable aprotic solvent, then further reducing the resulting acylated or alkylated reduced compound in an acidic medium with a suitable reducing agent; or acylating compounds of formula SVII with an electrophilic acylating agent in a suitable solvent, then reducing the resulting acylated compounds in an acidic medium with a suitable reducing agent.

7. A process according to claim 6, wherein the indol-3-yl-quinazolino-1,4-benzodiazepin-5,13-diones are suspended in a suitable solvent and reacted with a suitable salt-forming agent.

8. A process according to claim 6, wherein a suitable electrophilic acylating agent is p-nitrophenyl-2(S)-(1,1-dimethylethoxycarbonyl)amino-4-methylpentanoate, 2(S)-(1,1-dimethylethoxycarbonyl)-amino-4-methyl-pentanoic acid or p-nitrophenyl-2(S)-(benzyloxycarbonyl)amino-4-methylpentanoate; a suitable electrophilic alkylating agent is iodomethane or butyl-p-toluene sulfonate; a suitable aprotic solvent is N,N-dimethylformamide, acetonitrile, dimethylsulfoxide, tetrahydrofuran, or methylene chloride; a suitable acidic medium is acetic acid or trifluoroacetic acid; and a suitable reducing agent is sodium cyanoborohydride or triethylsilane.

9. A process according to claim 7, wherein a suitable solvent is water, methanol, ethanol, ethyl acetate or tetrahydrofuran and a suitable salt-forming agent is hydrochloric acid, hydrobromic acid, acetic acid, trifluoroacetic acid, propionic acid, succinic acid, lactic acid, isethionic acid, malic acid, tartaric acid, citric acid, stearic acid, toluenesulfonic acid, methanesulfonic acid, ethanedisulfonic acid or oxalic acid.

10. A pharmaceutical composition comprising an effective amount for antagonism of the function of cholecystokinins in mammals of one or more indol-3-yl-quinazolino-1,4-benzodiazepin-5,13-diones or pharmaceutically-acceptable salts of these derivatives, according to claim 1, and a pharmaceutically-acceptable carrier.

11. A pharmaceutical composition according to claim 10, wherein the indol-3-yl-quinazolino-1,4-benzodiazepin-5,13-diones comprise one or both members of the group consisting of 7-[(1-[2(R)-((1,1-dimethylethoxy)carbonyl)amino-4-methylpentanoyl]-2,3-dihydro-1H-indol-3-yl)methyl]quinazolino(3,2-A)-1,4-benzodiazepin-5,13-(5H,7H)-dione (isomer 1) and 7-[(1-[2(S)-((1,1-dimethylethoxy)carbonyl)amino-4-methylpentanoyl]-2,3-dihydro-1H-indol-3-yl)methyl]quinazolino(3,2-A)-1,4-benzodiazepin-5,13-(6H,7H)-dione.

12. A pharmaceutical composition according to claim 10, wherein the effective amount is from about 1 mg to about 1500 mg, administered in single or divided doses.

13. A pharmaceutical composition according to claim 12, wherein the effective amount is from about 10 mg to about 500 mg.

14. A pharmaceutical composition according to claim 10, wherein the mammals are humans.

15. A method of preventing or treating a mammal for disorders of the gastrointestinal, central nervous or appetite regulatory systems which comprises administering to said mammal a pharmaceutically-effective amount of one or more indol-3-yl-quinazolino-1,4-benzodiazepin-5,13-diones or pharmaceutically-acceptable salts thereof, according to claim 1.

16. A method according to claim 15, wherein a pharmaceutically-acceptable carrier is also administered.

17. A method according to claim 16, wherein the mammals are humans and a pharmaceutically-effective amount is from 1 mg to about 1500 mg, administered in single or divided doses.

* * * * *